US012303516B2

(12) United States Patent
Näsström et al.

(10) Patent No.: US 12,303,516 B2
(45) Date of Patent: *May 20, 2025

(54) METHODS AND FORMULATIONS FOR TREATMENT OF AND/OR PROTECTION AGAINST ACUTE LIVER FAILURE AND OTHER HEPATOTOXIC CONDITIONS

(71) Applicant: EGETIS THERAPEUTICS AB, Stockholm (SE)

(72) Inventors: Jacques Näsström, Bromma (SE); Sven Jacobsson, Stockholm (SE); Dennis Henriksen, Allerød (DK); James Van Alstine, Stockholm (SE)

(73) Assignee: Egetis Therapeutics AB, Stockholm (SE)

( * ) Notice: Subject to any disclaimer, the term of this patent is extended or adjusted under 35 U.S.C. 154(b) by 1 day.

This patent is subject to a terminal disclaimer.

(21) Appl. No.: 17/576,197

(22) Filed: Jan. 14, 2022

(65) Prior Publication Data

US 2022/0133739 A1 May 5, 2022

Related U.S. Application Data

(63) Continuation of application No. 16/068,626, filed as application No. PCT/IB2017/050115 on Jan. 10, 2017, now Pat. No. 11,260,060.

(60) Provisional application No. 62/361,605, filed on Jul. 13, 2016, provisional application No. 62/277,232, filed on Jan. 11, 2016.

(51) Int. Cl.
| | |
|---|---|
| A61P 1/16 | (2006.01) |
| A61K 9/08 | (2006.01) |
| A61K 9/10 | (2006.01) |
| A61K 9/19 | (2006.01) |
| A61K 31/167 | (2006.01) |
| A61K 31/198 | (2006.01) |
| A61K 31/555 | (2006.01) |
| A61K 31/6615 | (2006.01) |
| A61P 13/12 | (2006.01) |

(52) U.S. Cl.
CPC ............. *A61K 31/555* (2013.01); *A61K 9/08* (2013.01); *A61K 9/10* (2013.01); *A61K 9/19* (2013.01); *A61K 31/167* (2013.01); *A61K 31/198* (2013.01); *A61K 31/6615* (2013.01); *A61P 1/16* (2018.01); *A61P 13/12* (2018.01)

(58) Field of Classification Search
CPC .......... A61K 31/555; A61K 9/08; A61K 9/10; A61K 9/19; A61K 31/167; A61K 31/198; A61K 31/6615; A61P 1/16; A61P 13/12

See application file for complete search history.

(56) References Cited

U.S. PATENT DOCUMENTS

| | | | |
|---|---|---|---|
| 8,354,449 | B2 | 1/2013 | Goldstein |
| 2002/0142991 | A1 | 10/2002 | Herzenberg et al. |
| 2003/0069311 | A1 | 4/2003 | Herzenberg et al. |
| 2004/0142907 | A1 | 7/2004 | Batteux et al. |
| 2005/0070607 | A1 | 3/2005 | Andrus et al. |
| 2008/0139654 | A1 | 6/2008 | Soderling |
| 2010/0099762 | A1 | 4/2010 | Bush et al. |
| 2012/0101066 | A1 | 4/2012 | Karlsson et al. |
| 2014/0178358 | A1 | 6/2014 | Strigun et al. |
| 2015/0005259 | A1 | 1/2015 | Karlsson et al. |

FOREIGN PATENT DOCUMENTS

| | | |
|---|---|---|
| JP | 2005-508840 A | 4/2005 |
| JP | 2008-538586 A | 10/2008 |
| JP | 2010-507572 A | 3/2010 |
| JP | 2010-513229 A | 4/2010 |
| JP | 2012-532189 A | 12/2012 |
| JP | 2015-504066 A | 2/2015 |
| WO | 02/087579 A1 | 11/2002 |
| WO | 2011/004325 A1 | 1/2011 |
| WO | 2013/102806 A1 | 7/2013 |

OTHER PUBLICATIONS

Bedda et al., "Mangafodopir prevents liver injury induced by acetaminophen in the mouse," Journal of Hepatology 39 (2003) 765-772. (Year: 2003).*
Official Action from corresponding Japanese Application No. 2018555315, dated Nov. 25, 2020 with English Translation.
Woodhead, Jeffrey L. et al., An Analysis of N-Acetylcysteine Treatment for Acetaminophen Overdose Using a Systems Model of Drug-Induced Liver Injury, The Journal of Pharmacology and Experimental Therapeutics, 342(2):529-540 (2012).
Prescott, L.F. et al., The disposition and kinetics of intravenous N-acetylcysteine in patients with paracetamol overdosage, European Journal of Clinical Pharmacology, 37:501-506 (1989).

(Continued)

*Primary Examiner* — Jared Barsky
(74) *Attorney, Agent, or Firm* — Porter Wright Morris & Arthur LLP

(57) ABSTRACT

Methods for treating and/or protecting against acute liver failure and other hepatotoxicities in an individual employ a combination of a first active agent comprising N-acetylcysteine and a second active agent comprising a manganese complex selected from the group consisting of (i) a calcium manganese mixed metal complex of N,N'-bis-(pyridoxal-5-phosphate)-ethylenediamine-N,N'-diacetic acid (DPDP) having a molar ratio of calcium to manganese in a range of from 1 to 10, or a pharmaceutically acceptable salt thereof, (ii) a mixture of manganese DPDP (MnDPDP), or a pharmaceutically acceptable salt thereof, and a non-manganese-containing DPDP compound, or (iii) a mixture of manganese pyridoxyl ethylenediamine (MnPLED), or a pharmaceutically acceptable salt thereof, and a non-manganese-containing pyridoxyl ethylenediamine (PLED) compound.

21 Claims, 4 Drawing Sheets

(56) References Cited

OTHER PUBLICATIONS

Shi, Qiang et al., Circulating mitochondrial biomarkers for drug-induced liver injury, Biomarkers Med., 9(11):1215-1223 (2015).
Dear, Dr. James W., Target biomarker profile for the clinical management of paracetamol overdose, British Journal of Clinical Pharmacology, 80(3):351-362 (2015).
Laurent, Alexis et al., Controlling Tumor Growth by Modulating Endogenous Production of Reactive Oxygen Species, Cancer Research, 65(3):948-956 (2005).
Bedda Sassia et al., Mangafodipir prevents liver injury induced by acetaminophen in the mouse, Journal of Hepatology, 39:765-772 (2003).
Karlsson, Jan Olof G., Antioxidant activity of mangafodipir is not a new finding, Journal of Hepatology, 40:869-873 (2004).
Karlsson, Jan Olof G. et al., Calmangafodipir [Ca4Mn(DPDP)5], mangafodipir (MnDPDP) and MnPLED with special reference to their SOD mimetic and therapeutic properties, Drug Discovery Today, 20(4):411-421 (Apr. 2015).
Valko, Marian et al., Free radicals and antioxidants in normal physiological functions and human disease, The International Journal of Biochemistry & Cell Biology, 39:44-84 (2007).
Pieper, Galen M. et al., Protective Mechanisms of a Metalloporphyrinic Peroxynitrite Decomposition Catalyst, WW85, in Rat Cardiac Transplants, The Journal of Pharmacology and Experimental Therapeutics, 314(1):53-60 (2005).
Agarwal, Rakhee et al., Acetaminophen-Induced Hepatotoxicity in Mice Occurs with Inhibition of Activity and Nitration of Mitochondrial Manganese Superoxide Dismutase, The Journal of Pharmacology and Experimental Therapeutics, 337(1):110-116 (2011).
Thanacoody, H K R Ruben et. al., Scottish and Newcastle Antiemetic Pre-treatment for paracetamol poisoning study (SNAP), Pharmacology and Toxicology, 14(20):2050-6511 (2013).
Moore, Kevin, Renal failure in acute liver failure, European Journal of Gastroenterology & Hepatology, 11(9):967-975 (1999).
Chen, Yu-Guang et al, Risk of Acute Kidney Injury and Long-Term Outcome in Patients With Acetaminophen Intoxication, Medicine, 94(46):1-6 (Nov. 2015).
Smilkstein et al, New England Jouranl of Medicine, 319(24):1557-1562 (1988).
Rumack et al, Clinical Toxicology, 50:91-98 (2012).
Cairney et al, Clinical Toxicology, 54(5):405-10 (Published online: Apr. 25, 2016).
Mashkovskiy M.D. Lekarstvennyye sredstva [Drugs]. 14-ed., vol. 1, Moscow, p. 11 (2001), with English Translation.
Pharmaceutical Technology: Controlling Ice Nucleation During the Freezing Step of Lyophilization, vol. 37., No. 5., p. 36 (2013), with English Translation.
Official Action from corresponding Russian Application No. 2018128793, dated May 22, 2020, with English Translation.
Search Report from corresponding Russian Application No. 2018128793, dated May 22, 2020, with English Translation.
Official Action from corresponding Chinese Application No. 2017800062921, dated Sep. 3, 2020, with English Translation.
Mukhin N. et al. Possibilities of changing a prognosis in patients with an acute hepatic failure //Doctor, No. 4, pp. 17-21 (2009), refer to p. 2 of the Search Report dated May 22, 2020.
D.A. Kharkevich, Pharmacology, Moscow, Meditsina, pp. 47-48 (1987), refer to p. 9 of the Official Action dated May 22, 2020.
Fontana, MD, Robert J. et al., Acute Liver Failure including Acetaminophen Overdose, Med Clin North Am., vol. 92, No. 4, pp. 761-794 (Jul. 2008).
Lyophilization: A Primer, Pharmaceutical Technology Editors, vol. 37, No. 5, p. 1 (May 2, 2013).
Prescott et al, Intravenous N-acetylcysteine: the treatment of choice for paracetamol poisoning, British Medical Journal, 2:1097-1100 (1979).

\* cited by examiner

METHODS AND FORMULATIONS FOR TREATMENT OF AND/OR PROTECTION AGAINST ACUTE LIVER FAILURE AND OTHER HEPATOTOXIC CONDITIONS

FIELD OF THE INVENTION

The present invention is directed to methods and formulations for treatment of and/or protecting against acute liver failure and other hepatotoxic conditions, and associated renal injuries. The methods and formulations employ a first active agent which replenishes or decreases a loss of functional glutathione (GSH) in an individual, one example of which is N-acetylcysteine (NAC), and a second active agent comprising a manganese complex selected from a specified group, an example of which is a mixed metal complex of calcium and manganese, calmangafodipir, or a salt thereof.

BACKGROUND OF THE INVENTION

Paracetamol, also known in North America as acetaminophen and abbreviated as APAP, is known to induce acute liver failure (ALF) upon overdose. It is one of the most commonly used pharmaceuticals in the world and is often available without a doctor's prescription. Acetaminophen-induced ALF is characterized by massive hepatocyte cell death related to depletion of functional reduced glutathione (GSH). GSH is an important antioxidant in vivo and interacts with enzyme systems to prevent damage to important cellular components caused by reactive oxygen species. The ratio of reduced glutathione to oxidized glutathione (GS) within cells can be used to indicate the degree of cellular oxidative stress. Specifically, acetaminophen generates a reactive substance, N-acetyl-p-benzoquinone (NAPQI), which can conjugate with functional glutathione. Depletion of functional glutathione leads to enhanced oxidative stress, mitochondrial breakdown and dysfunction, and cell death, e.g., Hodgman and Garrard, *Crit. Came Clin.*, 28:499-516 (2012), Jaeschke et al, *Drug. Metab. Review*, 44:88-106 (2012).

Acetaminophen-induced liver cell damage is typically evidenced by release into the serum (i.e., serum activity) of liver intracellular enzymes such as aspartate aminotransferase (ASAT in Europe, or AST in the United States) or alanine aminotransferase (ALAT/ALT). ALF and overdosed patient risk for development of ALF is often monitored by measuring one or both of these enzymes in the serum. In 2009, acetaminophen overdoses were estimated to be responsible for approximately 80,000 emergency hospital visits, 33,000 hospital treatments, and 1000 deaths per year in the United States. Generally, when a suspected overdose patient presents for medical attention, the physician has to rapidly decide whether to monitor the patient or to begin treatment, which can range from simple charcoal ingestion, to stomach pumping, to NAC administration, to liver transplant surgery. Transplantation surgery can only be carried out in specialized hospitals and transport of a patient to a qualified facility may not be readily possible in advanced ALF.

The most common method of treatment of acetaminophen-induced ALF, both in the United States and Europe, involves administration of N-acetylcysteine (NAC). NAC is often administered by intravenous (IV) injection at a total dose of approximately 300 mg/kg, but such large doses can have disadvantageous side-effects. Additionally, NAC treatment of ALF often involves complicated dosing schedules. One NAC intravenous dosing schedule involves a loading dose of 150 mg/kg infused over 1 hour in 200 ml of 5% dextrose solution, followed by less physiologically challenging maintenance doses of 50 mg/kg in 500 mL dextrose solution over 4 hours, and then 100 mg/kg in 1000 mL of dextrose solution over 18 hours. Various other dosing regimens have been suggested, e.g., Thanacoody et al, *BMC Pharmacology and Toxicology*, 14:20 (2013), including less concentrated maintenance dosing over much longer time periods, e.g., up to several days. Across the various dosing regimens, however, NAC is only assuredly effective if given soon enough after an overdosing (OD) event for it to replenish depleted functional glutathione levels, which can often be difficult to achieve. The beneficial effect of NAC administration is thus initiation time-dependent and ALF due to acetaminophen overdose is encountered even in cases where treatment has been administered.

In practice, acetaminophen-induced ALF conditions of intoxication, and responses to them, vary tremendously. Woodhead et al, *The Journal of Pharmacology and Experimental Therapeutics*, 342:529-540 (2012), describes various NAC treatment regimens and also notes the controversy and varied opinion in regard to such regimens, monitoring approaches, and related factors.

Chemical conjugation of NAPQI with glutathione reduces the toxicity of NAPQI; however, if appreciable amounts of NAPQI are generated, this can lead to significant depletion of glutathione, which in turn can lead to mitochondrial dysfunction and cell death (Rushworth et al, *Pharmacology & Therapeutics*, 141:150-159 (2014)). NAC is readily transported into liver cells and functions to replenish glutathione levels in deficient cells, allowing cells to conjugate NAPQI and resist development of ALF. However, as intoxication proceeds along the above-noted path to a situation where mitochondrial and cell systems and structures are compromised, such that NAC cannot effectively replenish glutathione, the ability of NAC to prevent cell death is reduced. Variations in overdose situations and individual responses result in great disparity among patients in the post-OD time when NAC will start to show reduced efficacy.

Rushworth et al teach that NAC should not be considered a powerful antioxidant in its own right, as its benefit lies in the targeted replenishment of GSH in GSH-deficient cells. As such, conditions exist where NAC is not expected to be beneficial. Deeper insight to the biochemical role of NAC comes from Okezie et al., *Free Radical Biology and Medicine*, 6:593-597 (1989), which discloses that while NAC can react with hydroxy ($OH^-$) radicals and is a powerful scavenger of hypochlorous acid, it only reacts slowly with hydrogen peroxide ($H_2O_2$) and not appreciably with superoxide ($O_2^-$). As such, NAC is not catalytic and does not appear to significantly interact directly with two reactive oxygen species linked to oxidative stress related pathologies (although it may affect them indirectly via GSH generation).

Physicians typically make ALF-risk and -treatment decisions based on a wide range of data inputs, typically including monitoring a patient's ALT levels over time. NAC treatment is complicated and so may carry some procedural risk. NAC treatment, though used widely, is not ideal as represented by the significant variation in dosages, dosing regimens, methods of administration, methods of monitoring treatment, and controversy over how long to maintain treatment. Additionally, higher doses and/or longer NAC regimens carry a possible risk of impeding hepatic recovery and presenting undesirable side effects, as discussed by Prescott et al, *Eur. J. Clin. Pharmacol.*, 37:501-506 (1989).

Acetaminophen-induced ALF, and other ALF and hepatotoxic conditions are, in general, characterized by a failure of the body to handle disease-related or injury-related reactive oxygen species. Hepatotoxic conditions include hepatitis C, microbial infections, viral infections, and non-alcoholic steatohepatitis (NASH). They also include a wide variety of drug-induced liver injuries, including some related to modern medical treatments based on biopharmaceuticals such as monoclonal antibodies. In 2014, for example, the US FDA approved 41 new molecular entities and new therapeutic biological products, with over 15% of these including Warnings and Precautions in regard to risk of liver injury (Shi et al, *Biomarkers Med.*, 9(11):1215-1223 (2015)). Other major pharmaceuticals that may cause ALF include statins, nicotinic acid, Amiodarone (Cardarone), Nitrofurantoin, and Augmentin.

Shi et al (2015) and Dear et al, *The British Pharmacological Society*, 80(3):351-362 (2015), refer to circulating mitochondrial biomarkers for drug induced liver injury. A large number of various types of biomarkers (immunological, mitochondrial status, toxicogenetic, acetaminophen metabolic, and biochemical such as nitrated tyrosine residues) are known for ALF. Biomarkers are being used more and more in regard to diagnosis, monitoring, selection of treatment, and prognosis related to patient status as well as response to treatment. Given the acute but often varied onset nature of ALF, biomarkers hold promise to play a special role in regard to preventative treatments to reduce ALF conditions. In addition to Shi et al and Dear et al, see also Harrill et al, *Tox. Sciences*, 110:235-243 (2009), and Vliegenthart et al, *Clin. Pharmacol. Ther.* (doi: 10.1002/cpt.541, online Nov. 30, 2016). The latter article discusses possible use of biomarkers to stratify patients by risk of liver injury prior to starting NAC.

Acute kidney injury (AKI) occurs in approximately 55% of all patients who present with acute liver failure (ALF) (Moore, *Eur. J. Gastroenterol. Hepatol.*, 11(9):967-975 (1999)). In acetaminophen (APAP) overdose-induced ALF, renal injury may be related to complications which affect both the liver and kidneys, but, according to Moore, patients with renal injury will almost always recover if liver function can be recovered. A recent study of approximately 3000 cases of acetaminophen (APAP) overdose induced ALF concluded that the overall risk of such patients developing AKI was over two-fold higher than in controls (Chen et al, *Medicine*, 94(46):e2040 (2015)). While very few patients developed end-stage renal disease, Chen concluded that AKI is a possible adverse effect among patients with APAP intoxication, regardless of whether or not the patients presented with hepatic toxicity.

Reactive oxygen species (ROS)-related kidney pathologies are also known, and antioxidants have been tested in kidney-directed therapies where ROS may induce complications. Such treatments have included N-acetylcysteine (NAC) in conjunction with dialysis or for cirrhotic patients undergoing abdominal surgery. Rushworth at al also note that NAC has been tested in regard to protecting patients against contrast agent induced nephropathy and other diseases.

Manganese pyridoxyl ethylenediamine derivatives (also sometimes referred to as manganese pyridoxyl ethyldiamine derivatives), known as MnPLED-derivatives, have been disclosed as having beneficial catalase, glutathione reductase and SOD mimetic activities, Laurent et al, *Cancer Res*, 65:948-956 (2005). One such MnPLED derivative, mangafodipir, manganese N,N'-bis-(pyridoxal-5-phosphate)-ethylenediamine-N,N'-diacetic acid, also known as MnDPDP (CAS 146078-14-4), has been disclosed for protecting against and treating acetaminophen-induced ALF in mice, Bedda et al, *J Hepatol*, 39:765-772 (2003); Karlsson, *J Hepatol*, 40:872-873 (2004). MnDPDP is a manganese complex of fodipir, fodipir (Pubchem compound 60683, IUPAC Name: 2-[2-[carboxymethyl-[[3-hydroxy-2-methyl-5-(phosphonooxymethyl)pyridin-4-yl]methyl]amino]ethyl-[[3-hydroxy-2-methyl-5-(phosphonooxymethyl)pyridin-4-yl]methyl]amino]acetic acid). MnDPDP is dephosphorylated to an intermediate, MnDPMP, (manganese (II) N,N'-dipyridoxylethylenediamine-N,N'-diacetate-5-phosphate) and then to MnPLED (manganese (II) N,N'-dipyridoxylethylenediamine-N,N'-diacetate). This dephosphorylation is thought to occur mainly by alkaline phosphatases rather than acid phosphatases in serum, according to in vitro metabolic rates and in vivo activities.

The PledPharma AB WO 2011/004325 discloses that a mixture of a manganese complex compound such as mangafodipir and a non-manganese PLED-derivative compound such as N,N'-bis-(pyridoxal-5-phosphate)-ethylenediamine-N,N'-diacetic acid, also known as DPDP, can provide therapeutic advantages over mangafodipir alone in treating a variety of reactive oxygen species (ROS)-related disease conditions, including acetaminophen-induced ALF. Surprisingly, the mixture reduces the possibility of cerebral and other complications related to release of manganese from mangafodipir in the body. The PledPharma AB WO 2013/102806 discloses the use of calcium-manganese mixed metal PLED derivatives, and, specifically, calcium-manganese mixed metal complexes of N,N'-bis-(pyridoxal-5-phosphate)-ethylenediamine-N,N'-diacetic acid (DPDP). A specific calcium-manganese mixed metal complex of DPDP is calmangafodipir (CAS 1401243-67-1), also known as $Ca_4MnDPDP_5$, abbreviated herein as "CaM". CaM provides therapeutic advantages over mangafodipir alone in treating a variety of ROS-related disease conditions, including acetaminophen-induced ALF. The mixed metal complex calmangafodipir reduces the possibility of cerebral and other complications related to release of manganese from mangafodipir in the body and also provide important improvements in production, formulation, and therapeutic administration. See Karsson et al., *Drug Disc. Today* 20:411-421 (2015).

GSH is involved as a reagent in complex biochemical systems which include enzymes such as superoxide dismutase, catalase and glutathione reductase, which act to prevent oxidative stress (OS) caused by overproduction of reactive oxygen species (ROS) such as $OH^-$, $H_2O_2$ and $O_2^-$, as well as reactive nitrogen species (RNS) such as peroxynitrite ($ONOO^-$), Valko, *Int. J. Biochemistry & Cell Biology*, 39:44-84 (2007). The latter can covalently modify biological molecules including proteins via nitration or nitrosylation. Superoxide dismutase (SOD) enzymes are known to readily react with superoxide radicals and convert them to hydrogen peroxide which the enzyme catalase can convert to water and oxygen. Peroxynitrite plays a nefarious role in OS in general and particularly in ALF conditions such as acetaminophen overdose as it is able to react with a tyrosine residue in the active site of SOD, with the resulting nitration of the tyrosine residue compromising SOD enzymatic activity. This results in an increase of superoxide, as well as the formation of peroxynitrite, Agarwal, *J. Pharmacol. & Exp. Therapeutics*, 337:110-116 (2011). SOD enzyme catalytic activities are related to metal (typically Ni or Mn)-chelated cofactors and some compounds with metal chelating groups such as porphyrins are sometimes referred to "peroxynitrite decomposition agents or catalysts" (Pieper, *J. Pharmacol. & Exp. Therapeutics*, 314:53-60 (2005).

NAC is not the only reducing compound that is used or under investigation for replenishing intracellular glutathione levels under disease circumstances related to oxidative stress. Other compounds which have been studied include methionine and methionine analogues such as DL-methionine, D-methionine, N-acetyl-methionine (Garlick, *The Journal of Nutrition,* 136:1722S-1725S (2006)), N-acetyl-cysteine-amide (Wu et al, *Biomed. Chromatography,* 20:415-422 (2006)). Others include cysteine, homocysteine, glycyrrhizin, and GSH itself.

MnPLED compounds are known to have SOD catalytic mimetic properties and, in some cases, have also been found to have catalase and glutathione reductase mimetic activities (Karlsson, 2015). None of these enzymatic activities are associated with NAC or related chemical antioxidant compounds.

SUMMARY OF THE INVENTION

Additional improvements in treating and protecting against acetaminophen-induced ALF, other ALF conditions, and hepatotoxic conditions, including, but not limited to, those associated with administration of therapeutic agents which cause ALF, hepatitis C, microbial infections, viral infections, including but not limited to HIV infection, non-alcoholic steatohepatitis (NASH), and certain inherited disorders such as Wilson's Disease, and alpha-1-antitrypsin deficiency, are desired. The present invention is directed to methods and formulations for treating and/or protecting against ALF and other hepatotoxic conditions. In certain embodiments, the present invention is directed to methods and formulations for treating and/or protecting against AKI and related complications concomitant with ALF and other hepatotoxic conditions.

Within the context of the present disclosure, the term "protecting against" includes, in one embodiment, preventing, the indicated condition, and/or reducing the extent of development of the indicated condition, particularly in an individual at risk of development of the indicated condition.

In certain embodiments, the invention is directed to a method of treating and/or protecting against acute liver failure induced by an acetaminophen overdose in an individual. The method comprises (a) administering to the individual an effective amount of a first active agent which replenishes, or decreases a loss of, functional glutathione in the individual, and (b) administering an effective amount of a second active agent comprising a manganese complex and selected from the group consisting of (i) a calcium manganese mixed metal complex of N,N'-bis-(pyridoxal-5-phosphate)-ethylenediamine-N,N'-diacetic acid (DPDP) having a molar ratio of calcium to manganese in a range of from 1 to 10, or a pharmaceutically acceptable salt thereof, (ii) a mixture of manganese DPDP (MnDPDP), or a pharmaceutically acceptable salt thereof, and a non-manganese-containing DPDP compound, or (iii) a mixture of manganese pyridoxyl ethylenediamine (MnPLED), or a pharmaceutically acceptable salt thereof, and a non-manganese-containing pyridoxyl ethylenediamine (PLED) compound, to the individual.

In further embodiments, the invention is directed to a method of treating and/or protecting against acute liver failure in an individual. The method comprises (a) administering to the individual an effective amount of a first active agent which replenishes, or decreases a loss of, functional glutathione in the individual, and (b) administering an effective amount of a second active agent comprising a manganese complex and selected from the group consisting of (i) a calcium manganese mixed metal complex of DPDP having a molar ratio of calcium to manganese in a range of from 1 to 10, or a pharmaceutically acceptable salt thereof, (ii) a mixture of MnDPDP, or a pharmaceutically acceptable salt thereof, and a non-manganese-containing DPDP compound, or (iii) a mixture of MnPLED, or a pharmaceutically acceptable salt thereof, and a non-manganese-containing PLED compound, to the individual.

In yet further embodiments, the invention is directed to a method of treating and/or protecting against hepatotoxicity in an individual. The method comprises (a) administering to the individual an effective amount of a first active agent which replenishes, or decreases a loss of, functional glutathione in the individual, and (b) administering an effective amount of a second active agent comprising a manganese complex selected from the group consisting of (i) a calcium manganese mixed metal complex of DPDP having a molar ratio of calcium to manganese in a range of from 1 to 10, or a pharmaceutically acceptable salt thereof, (ii) a mixture of MnDPDP, or a pharmaceutically acceptable salt thereof, and a non-manganese-containing DPDP compound, or (iii) a mixture of MnPLED, or a pharmaceutically acceptable salt thereof, and a non-manganese-containing PLED compound, to the individual.

In further embodiments, the invention is directed to a method of reducing acute kidney injury associated with acute liver failure or other hepatotoxicity in an individual. The method comprises (a) administering an effective amount of a second active agent comprising a manganese complex selected from the group consisting of (i) a calcium manganese mixed metal complex of DPDP having a molar ratio of calcium to manganese in a range of from 1 to 10, or a pharmaceutically acceptable salt thereof, (ii) a mixture of MnDPDP, or a pharmaceutically acceptable salt thereof, and a non-manganese-containing DPDP compound, or (iii) a mixture of MnPLED, or a pharmaceutically acceptable salt thereof, and a non-manganese-containing PLED compound, to the individual, and optionally (b) administering to the individual an effective amount of a first active agent which replenishes, or decreases a loss of, functional glutathione in the individual.

In yet further embodiments, the invention is directed to a therapeutic method of administering a high dosage of acetaminophen to an individual. The method comprises administering a therapeutic high dosage of acetaminophen to the individual, and administering an effective amount of a second active agent comprising a manganese complex selected from the group consisting of (i) a calcium manganese mixed metal complex of DPDP having a molar ratio of calcium to manganese in a range of from 1 to 10, or a pharmaceutically acceptable salt thereof, (ii) a mixture of MnDPDP, or a pharmaceutically acceptable salt thereof, and a non-manganese-containing DPDP compound, or (iii) a mixture of MnPLED, or a pharmaceutically acceptable salt thereof, and a non-manganese-containing PLED compound, to the individual. Optionally, the method may also include administering to the individual an effective amount of a first active agent which replenishes, or decreases a loss of, functional glutathione in the individual.

In further embodiments, the invention is directed to a formulation comprising a first active agent which replenishes, or decreases a loss of, functional glutathione in an individual, and a second active agent comprising a manganese complex selected from the group consisting of (i) a calcium manganese mixed metal complex of DPDP having a molar ratio of calcium to manganese in a range of from 1 to 10, or a pharmaceutically acceptable salt thereof, (ii) a mixture of MnDPDP, or a pharmaceutically acceptable salt thereof, and a non-manganese-containing DPDP compound, or (iii) a mixture of MnPLED, or a pharmaceutically acceptable salt thereof, and a non-manganese-containing PLED compound. In yet further embodiments, the invention is directed to a kit containing at least one such formulation.

The methods, formulations and kits provide improvements in treating and/or protecting against ALF and other hepatotoxic conditions.

BRIEF DESCRIPTION OF THE DRAWINGS

The following detailed description and the Examples will be more fully understood in view of the drawings, in which.

DETAILED DESCRIPTION

Figure 1:
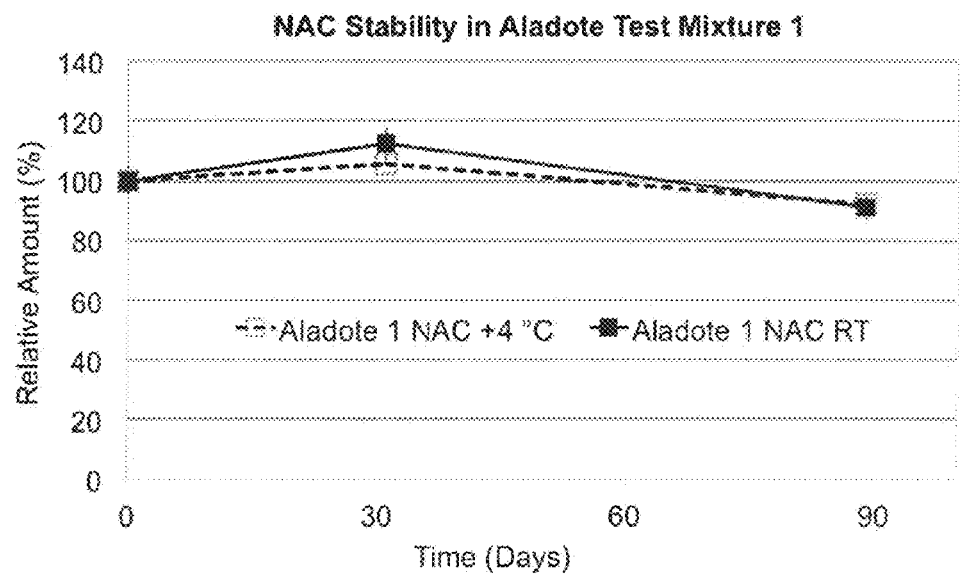
FIG. 1 shows the relative reduction of N-acetylcysteine (NAC) concentration versus storage time of NAC:CaM Test Mixture 1 at room temperature (RT, 22° C.) and +4° C. as described in Example 2.
Figure 2:
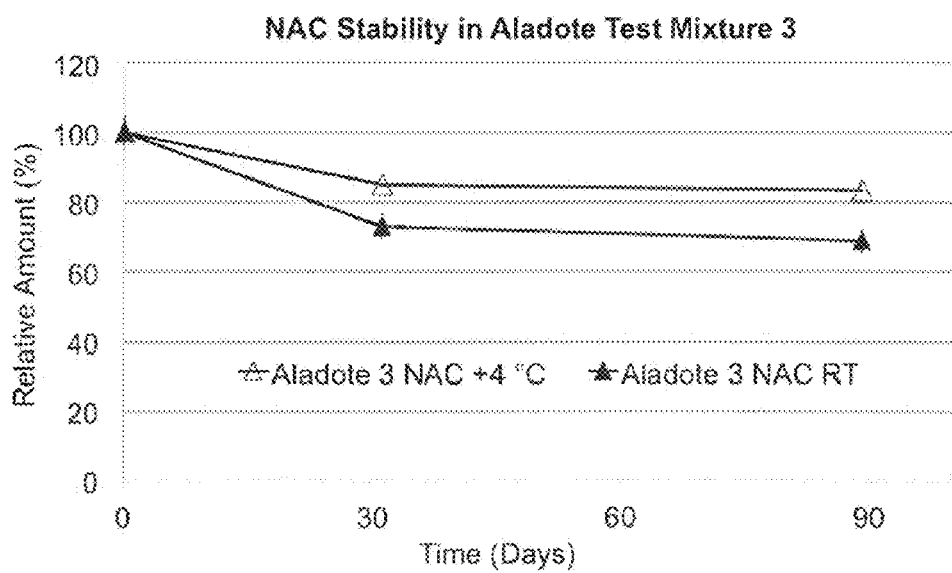
FIG. 2 shows the relative reduction in N-acetylcysteine (NAC) concentration versus storage time of NAC:CaM Test Mixture 3 at room temperature (RT, 22° C.) and +4° C., as described in Example 2.
Figure 3:
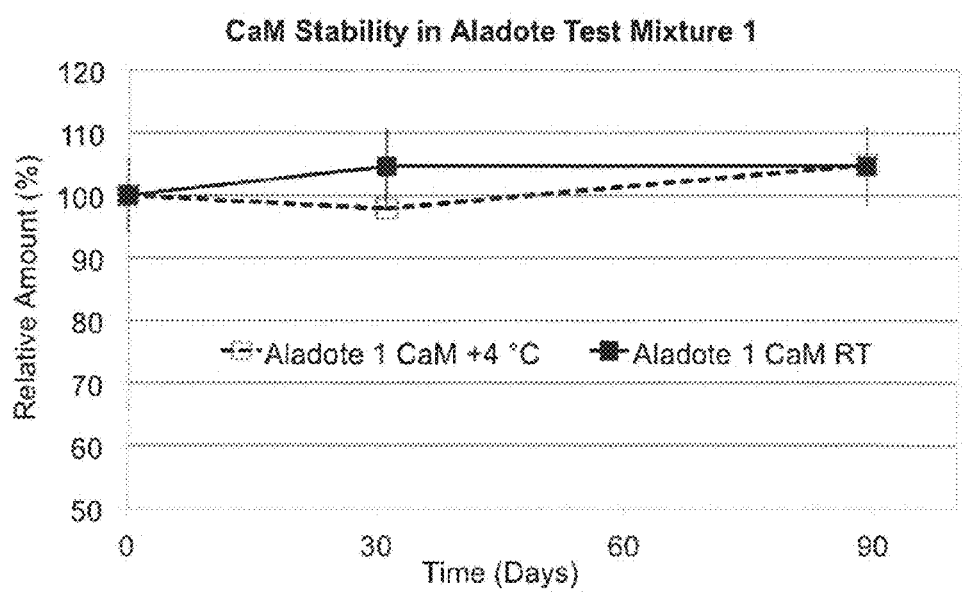
FIG. 3 shows the relative reduction in calmangafodipir (CaM) concentration versus storage time of NAC:CaM Test Mixture 1 at room temperature (RT, 22° C.) and +4° C., as described in Example 2.
Figure 4:
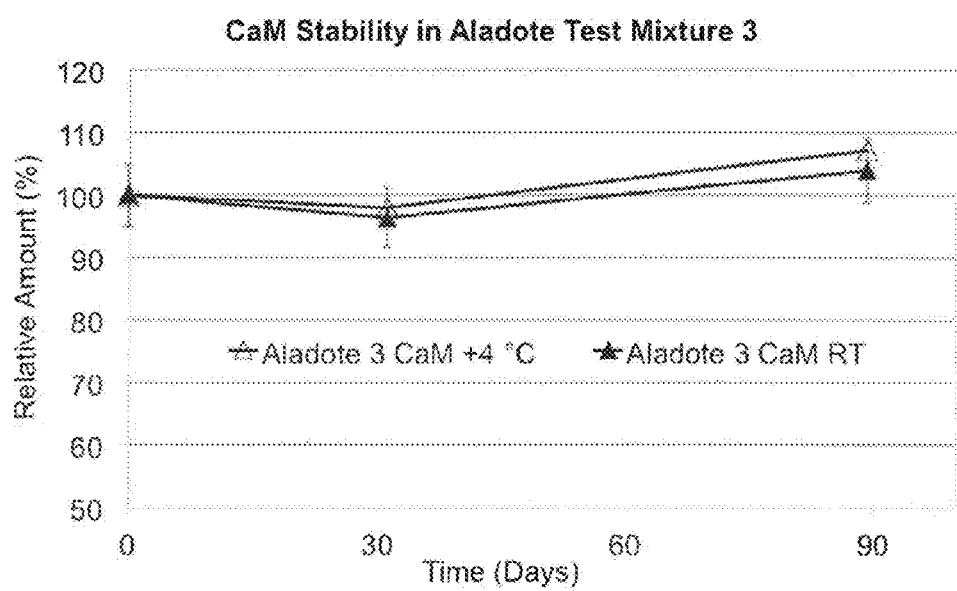
FIG. 4 shows the relative reduction in calmangafodipir (CaM) concentration versus storage time of NAC:CaM Test Mixture 3 at room temperature (RT, 22° C.) and +4° C., as described in Example 2.

In certain embodiments, the methods, formulations and kits of the invention employ a first active agent and a second active agent. The first active agent and the second active agent may be administered together or separately, as discussed in further detail below. The first active agent replenishes, or decreases a loss of, functional glutathione in the individual, i.e., restores or assists in restoring functional glutathione to a normal range, such as that experienced in a healthy individual. Functional glutathione is glutathione (in any form) which functions in vivo, preventing damage to cellular components, such as by covalently reacting with NAPQI to render it less toxic. The first active agent may be administered in an effective amount, i.e., an amount effective to at least partially replenish, or decrease a loss of, functional glutathione in the individual which has occurred owing to acetaminophen overdose or other hepatotoxicity-inducing event or condition. In a specific embodiment, the first active agent comprises N-acetylcysteine (NAC), cysteine, homocysteine, glycyrrhizin, GSH, methionine, a methionine analogue (DL-methionine, D-methionine, and/or N-acetyl-methionine), N-acetyl-cysteine-amide, or a combination thereof. In a more specific embodiment, the first active agent comprises NAC.

A specific effective dosage of the first active agent for a particular patient may be determined by one of ordinary skill in the art in view of the present disclosure. In a specific embodiment, wherein the first active agent comprises NAC, cysteine, homocysteine, glycyrrhizin, GSH, methionine, or a combination thereof, the first active agent, or, specifically, NAC, may be administered in a total dosage amount of 100-500 mg/kg body weight, in accordance with current conventional treatment therapies, typically administered with an initial/loading dosing regimen of 150 mg/kg, followed by maintenance dosages of 50 to 100 mg/kg. However, in certain embodiments of the inventive methods and formulations, wherein the first active agent comprises NAC, cysteine, homocysteine, glycyrrhizin, GSH, methionine, or a combination thereof, the first active agent, or, specifically, NAC, may be employed in an amount less than that conventionally employed. For example, the first active agent, or, specifically, NAC, may be administered in a total dosage of from about 10 to 200 mg/kg body weight, or, more specifically, from about 10 to 150 mg/kg body weight, from about 10 to 100 mg/kg body weight, or from about 10 to 50 mg/kg body weight. The total dosage may be administered in a single administration or in an initial administration followed by one or more additional administrations. Therefore, these embodiments are advantageous in employing a lower level of the first active agent as compared with various conventional NAC treatment methods.

The second active agent comprises a manganese complex which exhibits SOD mimetic activity, and, optionally, catalase, glutathione reductase and/or other mimetic activity. The manganese complex is selected from the group consisting of (i) a calcium manganese mixed metal complex of N,N'-bis-(pyridoxal-5-phosphate)-ethylenediamine-N,N'-diacetic acid (DPDP) having a molar ratio of calcium to manganese in a range of from 1 to 10, or a pharmaceutically acceptable salt thereof, (ii) a mixture of manganese DPDP (MnDPDP), or a pharmaceutically acceptable salt thereof, and a non-manganese-containing DPDP compound, or (iii) a mixture of manganese pyridoxyl ethylenediamine (MnPLED), or a pharmaceutically acceptable salt thereof, and a non-manganese-containing pyridoxyl ethylenediamine (PLED) compound, to the individual. Within the present disclosure, calmangafodipir refers to a calcium-manganese mixed metal complex of MnDPDP, containing an approximate calcium to manganese molar ratio of 4:1, also known as $Ca_4MnDPDP_5$, abbreviated herein as "CaM". Calmangafodipir is disclosed in WO 2013/102806 A1, which is incorporated herein in its entirety. In a specific embodiment, the second active agent comprises calmangafodipir.

Within the present disclosure, the term "a non-manganese-containing DPDP compound" refers to N,N'-bis-(pyridoxal-5-phosphate)-ethylenediamine-N,N'-diacetic acid (DPDP), a metal complex of DPDP which does not contain manganese, i.e., a calcium complex, or a pharmaceutically acceptable salt of DPDP or of such a metal complex. In a specific embodiment, the molar ratio of the non-manganese-containing DPDP compound to MnDPDP, or pharmaceutically acceptable salt thereof, is in a range of from 1 to 10. In a specific embodiment, the mixture of MnDPDP, or a pharmaceutically acceptable salt thereof, and a non-manganese-containing DPDP compound comprises MnDPDP and CaDPDP, or salts thereof.

Further, within the present disclosure, the term "a non-manganese-containing PLED compound" refers to pyridoxyl ethylenediamine (PLED), a metal complex of PLED which does not contain manganese, i.e., a calcium complex, or a pharmaceutically acceptable salt of PLED or of such a metal complex. In a specific embodiment, the molar ratio of the non-manganese-containing PLED compound to MnPLED, or pharmaceutically acceptable salt thereof, is in a range of from 1 to 10. In a specific embodiment, the mixture of MnPLED, or a pharmaceutically acceptable salt thereof, and a non-manganese-containing PLED compound comprises MnPLED and CaPLED, or salts thereof.

Suitable pharmaceutically acceptable salts of the mentioned DPDP- and PLED-containing compounds (both those containing manganese, and those not containing manganese) include, but are not limited to, sodium salts, with one or more hydrogen ions replaced by sodium. Without wishing to be bound by theory, it is believed that both CaM and MnDPDP, and salts thereof, are pro-drugs in the sense that they metabolize in vivo into related PLED derivatives such as MnPLED.

The second active agent is employed in an effective amount. i.e., an amount effective to reduce the oxidative stress in the individual which occurred owing to acetaminophen overdose, or other hepatotoxicity-inducing event or condition, through SOD mimetic activity, and/or other activity, for example, catalase, glutathione reductase, and/or other activity. In certain embodiments, the second active agent may improve the effectiveness of the first active agent. A specific effective dosage of the second active agent for a particular patient may be determined by one of ordinary skill in the art in view of the present disclosure. In a specific embodiment, the second active agent is administered in a dosage of from about 0.01 to 50 mg/kg body weight, from about 0.1 to 25 mg/kg body weight, or from about 0.1 to 10 mg/kg body weight. In a more specific embodiment, calmangafodipir is administered in a dosage of from about 0.01 to 50 mg/kg body weight, from about 0.1 to 25 mg/kg body weight, or from about 0.1 to 10 mg/kg body weight. In another specific embodiment, a mixture of MnDPDP, or a salt thereof, and a non-manganese containing DPDP compound is administered in a dosage of from about 0.01 to 50 mg/kg body weight, from about 0.1 to 25 mg/kg body weight, or from about 0.1 to 10 mg/kg body weight. In another specific embodiment, a mixture of MnPLED, or a salt thereof, and a non-manganese containing PLED compound is administered in a dosage of from about 0.01 to 50 mg/kg body weight, from about 0.1 to 25 mg/kg body weight, or from about 0.1 to 10 mg/kg body weight.

The above and other embodiment dosage ranges disclosed herein generally reflect the wide range of patients, patient states, diseases, regionally recommended therapies, first active agents, and dosing regimens in which the present invention may find successful application.

As noted, acetaminophen-induced liver cell damage is typically evidenced by release into the serum (i.e., serum activity) of liver intracellular enzymes such as aspartate aminotransferase (ASAT in Europe, or AST in the United States) or alanine aminotransferase (ALAT/ALT). ALF is often monitored by measuring one or both of these enzymes in the serum. Accordingly, in the methods and compositions of the invention, an effective amount includes an amount which reduces serum ALAT and/or ASAT.

According to one embodiment of the invention, a method of treating acute liver failure induced by an acetaminophen overdose in an individual comprises (a) administering to the individual an effective amount of a first active agent which replenishes, or decreases a loss of, functional glutathione in the individual, and (b) administering an effective amount of a second active agent selected from the group consisting of (i) a calcium manganese mixed metal complex of DPDP having a molar ratio of calcium to manganese in a range of from 1 to 10, or a pharmaceutically acceptable salt thereof, (ii) a mixture of MnDPDP, or a pharmaceutically acceptable salt thereof, and a non-manganese-containing DPDP compound, or (iii) a mixture of MnPLED, or a pharmaceutically acceptable salt thereof, and a non-manganese-containing PLED compound, to the individual. The inventive method is particularly advantageous for use in situations in which an individual may not currently have received immediate treatment for an acetaminophen overdose and/or in which conventional NAC treatment is either not yet started, for example, if the individual is being monitored for impending ALF or the overdose-induced ALF has progressed to a point at which conventional NAC treatment alone may not be as effective as desired. In a specific embodiment, prior to administration of the first active agent or the second active agent, the individual will have been determined to be in need of a treatment to reduce the probability of oxidative stress leading to hepatocyte cell death. Such a determination may be made according to conventional techniques, for example, by monitoring serum ALAT and/or ASAT levels or more advanced techniques such as by monitoring biomarkers, for example, mitochondrial biomarkers (see Shi et al 2015, noted above). The method may therefore comprise determining a level of at least one biomarker indicative of acute liver failure induced by an acetaminophen overdose. Suitable biomarkers may include, but are limited to one or more of, paracetamol-protein adducts (for example, paracetamol-cysteine), microRNA-122 (miR-122), keratin-18 (K-18), high-mobility group box-1 (HMGB1), glutamate dehydrogenase, and mitochondrial DNA fragments such as kidney injury molecule-1 (KIM-1), as discussed by Dear et al 2015. Employing both the first active agent and the second active agent may provide longer therapeutic effect as compared with conventional NAC treatment, as NAC therapeutic benefit is expected to stop soon after NAC administration is discontinued. This has been shown to not be the case for the second active agent comprising a SOD enzymatic mimetic such as CaM or MnDPDP, which can provide extended therapeutic treatment of oxidative stress in vivo after administration. Employing the first and the second active agent may offer other therapeutic effects such as reduced chance of underdosing and also synergistic efficacy enhancements which are not simply additive in nature. The latter is discussed in more detail below.

The weight ratio of the first active agent to the second active agent may vary as desired. In specific embodiments, the weight ratio of the first active agent to the second active agent is in a range of from 300:1, 250:1, 200:1, or 150:1 to 1:1, from 100:1 to 1:1, from 50:1 to 1:1, from 20:1 to 1:1, or from 10:1 to 1:1. In one specific embodiment, a typical NAC to calmangafodipir (CaM) ratio (w/w) of 30 is used (e.g., NAC 150 mg/kg and CaM 5 mg/kg). In another specific embodiment, a typical NAC to CaM ratio (w/w) of 6 is used (e.g., NAC 30 mg/kg and CaM 5 mg/kg).

Without wishing to be bound by theory, the first active agent is a "stoichiometric" compound which replenishes a depleted functional glutathione level and is expected to be consumed or otherwise altered as it functions in vivo, such as during conjugation to NAPQI. On the other hand, the second active agent acts catalytically through its superoxide dismutase (SOD) or related enzyme mimetic activity. Additionally, the first active agent and the second active agent may not only exhibit different mechanisms for reducing reactive oxygen species (ROS), and affect different ROS targets, but they may act at different cellular sites. For example, NAC is quite hydrophilic, and though actively transported into cells, it may be expected to be less able to passively partition into and through lipid membranes than the more lipophilic MnPLED metabolic products resulting from Calmangafodipir, MnDPDP or MnPLED administration.

Different types of compounds such as antioxidants function via different mechanisms at different cellular sites. Use of combinations of antioxidants to treat various diseases has therefore been suggested. However, a combination of antioxidants cannot be assumed to function in vivo as desired due to several practical reasons. A mixture of two antioxidants may, for example, form an insoluble complex, chemically react to form a third non-functional compound, chemically alter (i.e., reduce or oxidize) each other in a manner to render one or both of them non-functional, and/or affect the patient in a manner to reduce the efficacy and/or enhance the toxicity of one or both antioxidants. The present inventors have discovered that a mixture of the first active agent and the second active agent, particularly, NAC and MnPLED or a MnPLED derivative compound such as calmangafodipir or MnDPDP, remains stable, as is demonstrated in Examples 1 and 2, and is efficacious, as demonstrated in Example 4.

In the methods of the invention, the first active agent and the second active agent may be substantially simultaneously administered to the individual, in one or separate formulations, or may be administered sequentially, for example with less than 1 hour, or 1, 2, 3, 4, 5, 6, 7, 8, 9, 10 or more hours between administrations. The second active agent may be administered to the individual subsequent to administration of the first active agent or, alternatively, prior to administration of the first active agent. The active agents may be administered in one or more formulations in solution form or in a freeze-dried formulation, or in other conventional pharmaceutically acceptable forms, optionally including one or more conventional pharmaceutical excipients or carriers. Calmangafodipir and mixtures of MnDPDP and other DPDP compounds are advantageously deliverable with water-soluble carriers. As MnPLED and various PLED compounds are relatively more hydrophobic in nature, formulations of these mixtures may advantageously include one or more excipient additives, including but not limited to, surfactants, micelles, or liposomes, to present the active components of the mixture in a less lipophilic (less hydrophobic) state and thus more suitable for delivery intravenously in a water-soluble formulation.

Various dosing regimens may also be employed wherein administration of the first active agent and the second active agent are alternated, or substantially simultaneous administration is followed by one or more individual administrations. For example, an additional dosage of the second active agent may be administered subsequent to a substantially simultaneous administration of the first active agent and the second active agent. In a specific embodiment, at least one of the first active agent and the second active agent are administered to the individual at a time 8 hours or more subsequent to the acetaminophen overdose. In a more specific embodiment, the second active agent is administered to the individual at a time 8 hours or more subsequent to the acetaminophen overdose. It is recognized however that the degree or time of an overdose occurrence is not always established at the time an individual is presented for treatment, so a physician may elect to begin treatment prior to or while conducting one or more laboratory tests to determine the degree or timing of an overdose.

In a further embodiment, several rounds of the first agent may be administered to the individual, with and/or alternating with administration of the second agent. In a specific embodiment, a first administration of the first agent is followed by an administration of the second agent, which, in turn is followed by a second administration of the first agent. The administration of the second agent may be closer in time to either the first administration or the second administration of the first agent, or may be spaced substantially equally in time therebetween.

In a specific embodiment, a formulation according to the invention comprises both the first active agent and the second active agent. The weight ratio of the first active agent and the second active agent may be varied as desired. In specific embodiments, the weight ratio of the first active agent and the second active agent is in a range of from 300:1, 250:1, 200:1, or 150:1 to 1:1, from 100:1 to 1:1, from 50:1 to 1:1, or from 20:1 to 1:1. The amount of the first active agent, or, specifically, NAC, in the formulation may be sufficient to provide a dosage of from about 10 to 300 mg/kg body weight. The amount of the second active agent, or, more specifically, calmangafodipir, in the formulation may be sufficient to provide a dosage of from about 0.01 to 50 mg/kg body weight, from about 0.1 to 25 mg/kg body weight, or from about 0.1 to 10 mg/kg body weight. The formulation may be in solution form, a dispersion or emulsion form, or a solid form, including a tablet or powder, and may comprise a freeze-dried formulation.

This embodiment of the invention may be particularly advantageous for facilitating treatment of acetaminophen overdose related to a single dosage event. Further, in more specific embodiments, the formulation comprises the first active agent, or, specifically, NAC, in an amount of from about 10 to 200 mg/kg body weight, or, more specifically, from about 10 to 150 mg/kg body weight, from about 10 to 100 mg/kg body weight, or from about 10 to 50 mg/kg body weight. Therefore, these embodiments are advantageous in employing a lower level of the first active agent as compared with various conventional NAC treatment methods, thereby providing treatment with a simple and more benign (less adverse side effects) dosing regimen. This may be particularly advantageous during any initial monitoring period in which the extent of overdose and related damage is not yet established and, if necessary, could be followed by a more aggressive treatment with the first active agent and/or the second active agent. Further, as noted above, a single formulation of the first active agent and the second active agent may provide longer therapeutic effect, as compared with conventional NAC treatment, as NAC therapeutic benefit is expected to stop soon after NAC administration is discontinued. This has been shown to not be the case for the second active agent SOD mimetics such as CaM and MnDPDP, which provide extended therapeutic treatment of oxidative stress in vivo after administration. Therefore, the combination formulations should provide improved treatments.

In another embodiment, the invention is directed to a kit for treating acute liver failure. The kit comprises at least one formulation as described, and at least one separate, i.e., separately packaged, formulation comprising the second active agent. Alternatively, the kit may comprise at least one formulation as described and one or more additional formulations of the first active agent. Further embodiments may include at least one formulation as described and one or more formulations of both the first active agent and the second active agent in relative amounts which vary from those in the at least one formulation. The kit may also include instructions for administration of the formulation(s) and/or instructions for selection of one or more formulations for administration to a patient from several formulations in the kit.

In another embodiment, the invention is directed to a method of treating acute liver failure comprising administering the first active agent to the individual and administering the second active agent to the individual. In another embodiment, the invention is directed to a method of treating hepatotoxicity, comprising administering the first active agent to the individual and administering the second active agent to the individual. In these additional embodiments, the ALF or hepatotoxicity may be the result of acetaminophen overdose or other hepatotoxic conditions, including, but not limited to, those associated with administration of other therapeutic agents which cause ALF, hepatitis C, microbial infections, viral infections, including but not limited to HIV infection, and/or NASH. Additionally, the dosing amounts, regimen variations and formulations discussed above may be equally applied in these methods.

In another embodiment, the invention is directed to a method of administering a therapeutic high dosage of acetaminophen to an individual, comprising administering a therapeutic high dosage of acetaminophen to the individual, and administering the second active agent to the individual in an amount effective to reduce or protect against liver damage by the high dosage of acetaminophen. Such methods are advantageous where a high dosage of acetaminophen is desirable, for example, for acute pain or acute fever, but would otherwise be avoided owing to the concomitant toxic effect. The second active agent dosing amounts discussed above may be equally applied in this method. Optionally, the methods may also include administration of the first active agent as described herein, and the dosing amounts, regimen variations and formulations discussed above for the first active agent may be equally applied in such methods.

The following Examples demonstrate various aspects of the invention.

Example 1

This Example describes short and long term stability studies involving mixtures of Calmangafodipir and NAC. Each mixture was formed by adding CaM (in the form of a trisodium salt powder) and NAC to deionised water and mixing on a Vortex shaker. The solution was then transferred to an amber vial. In these studies, typically no additives or stabilizers were used. Standard degradation studies undertaken at short term used the known method of "forced" temperature degradation by storing solutions at 70° C. for 6 hours (to indicate general longer-term storage performance). Samples were withdrawn at specified time points and analyzed by standard spectroscopic methods for N-acetylcysteine (NAC), Calmangafodipir (CaM) and Calmangafodipir-related substances. The concentration of NAC remained constant during the test, suggesting that this compound should be relatively stable in solutions with CaM. CaM showed a slight decrease in concentration (about 1% per hour).

Example 2

Long Term Stability Tests, involved two test mixtures. Mixture 1 comprised NAC, 10.4 mg/ml, plus CaM, 7.5 mg/ml (Mixture 1: NAC/CaM w/w ratio of 1.39) in 20 ml deionized water, and Mixture 3 comprised NAC, 10.4 mg/ml, plus CaM, 74.5 mg/ml (Mixture 3: NAC/CaM w/w ratio of 0.14). The test mixtures were studied for 3 months (90 days) at room temperature (RT, 22° C.) or 4° C. These are more realistic storage conditions for pharmaceutical products although, in the present studies, no common pharmaceutical formulation excipients were added to enhance CaM or NAC stabilization, and the storage vials were not sealed under nitrogen to reduce any effects of trapped oxygen. As such, these studies offer insight to results expected under less than optimal standard pharmaceutical storage conditions.

Concentrations of NAC and CaM were followed spectroscopically, as was the concentration of N,N'-diacetylcystine (diNAC), a self-oxidized (cystine, thiol R—S—S—R) form of NAC (R—SH).

Figure 5:
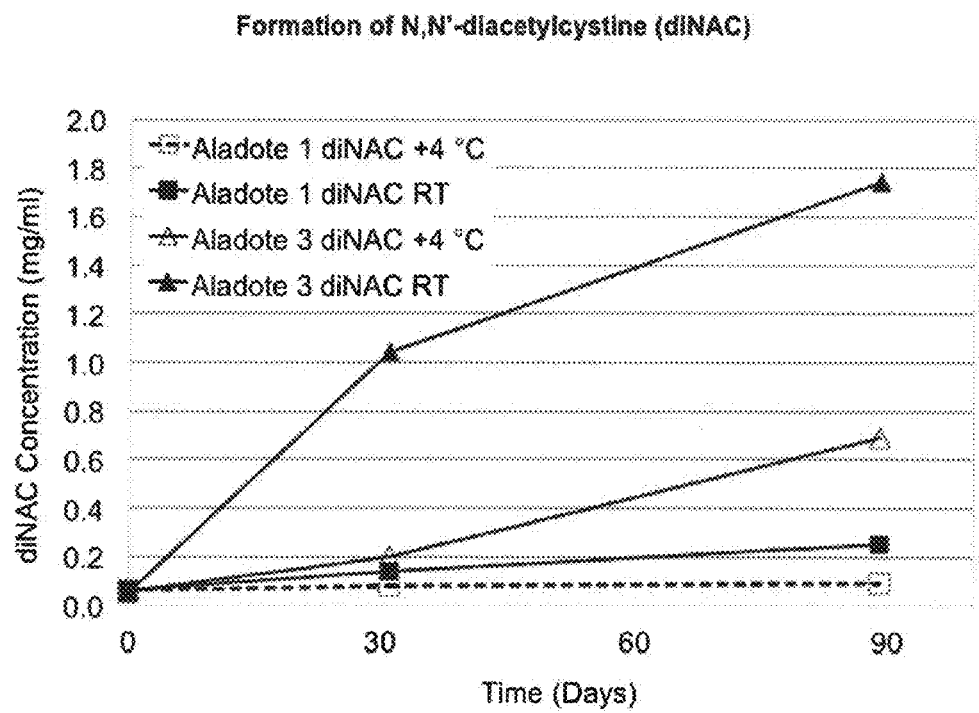
FIG. 5 shows the formation of N,N'-diacetylcystine (di-NAC) versus storage time of NAC:CaM Test Mixtures 1 and 3 at room temperature (RT, 22° C.) and +4° C., as described in Example 2.

FIGS. 1 to 4 show NAC and CaM storage solution concentration versus storage time (T), with the data normalized to 100% at T=0 due to slight variations in exact initial concentrations. In FIGS. 1-4, Mixtures 1 and 3 described above are indicated as Aladote Test Mixture 1 and Aladote Test Mixture 3, respectively. Typical error bars are also shown. FIG. 5 shows diNAC formation versus storage time. The figures indicate: (a) NAC is stable in NAC:CaM Test Mixture 1 at both 4° C. and 22° C. (FIG. 1), (b) There is apparently some depletion in NAC in Test Mixture 3 at both 4° C. (20% over 90 days) and at 22° C. (30% over 90 days) (FIG. 2), (c) CaM is stable at both 22° C. and 4° C. storage for both Test Mixture 1 (FIG. 3) and Test Mixture 3 (FIG. 4), (d) Some of the depletion of NAC in Test Mixture 3, particularly at 22° C. storage, appears to be due to diNAC formation (FIG. 5).

Example 3

This Example shows ALF response to acetaminophen-induced ALF mouse model studies based on accepted acetaminophen concentrations and methodologies. In each experiment, an i.p. injection of 300 mg/kg acetaminophen was made to male B6C3F1 mice to cause acetaminophen-induced ALF. In a first experiment, a 300 mg/kg dosage of NAC was administered 1-6 hours after acetaminophen administration. In a second experiment, NAC was administered in a dosage of 30-300 mg/kg NAC 1 hour after acetaminophen administration. In a third experiment, a dosage of 0.3-10 mg/kg calmangafodipir (CaM) was administered 6 hours post acetaminophen administration. In each experiment, ALAT was measured 12 hours following the i.p. injection of 300 mg/kg acetaminophen.

Figure 6:
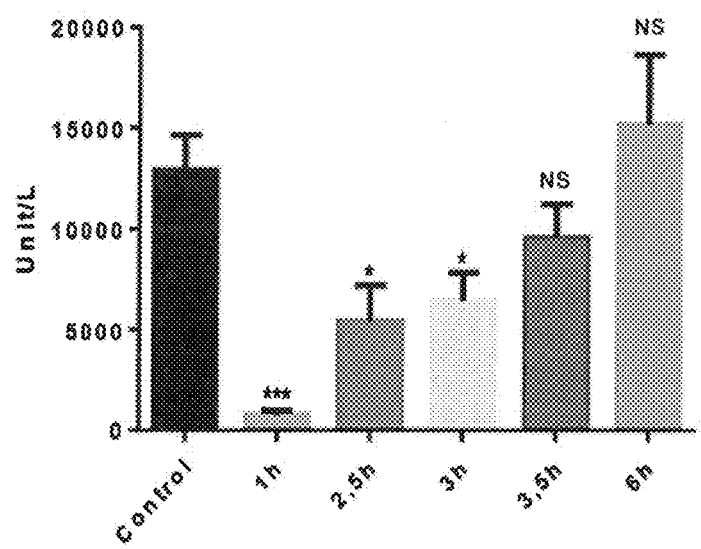
FIG. 6 shows the mean±SEM alanine aminotransferase (ALAT) levels at 12 hours following the i.p. injection of 300 mg/kg acetaminophen in male B6C3F1 mice (n=4-32 per bar), which also received 300 mg/kg NAC 1-6 hours after acetaminophen administration, as described in Example 3.
Figure 7:
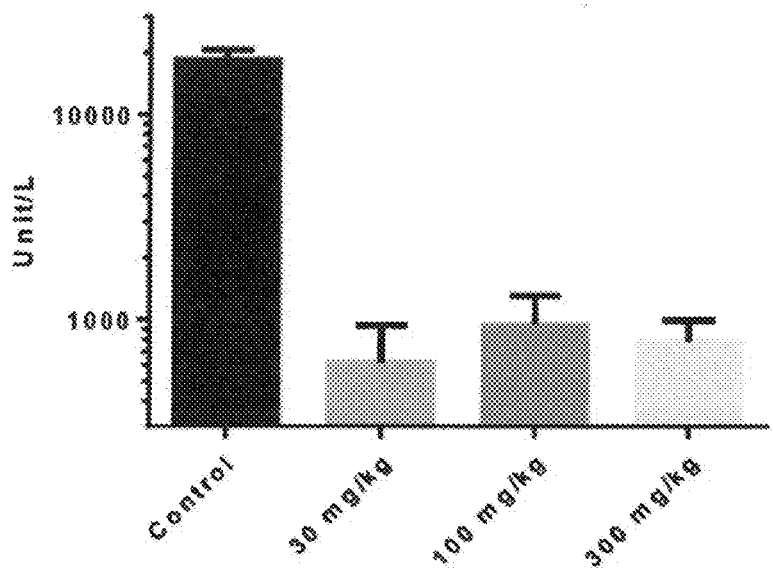
FIG. 7 indicates the mean t SEM ALAT levels at 12 hours following i.p. injection of 300 mg/kg acetaminophen in male 86C3F1 mice which were also administered a NAC dosage of 30-300 mg/kg NAC 1 hour post acetaminophen administration (n=4-11 per bar), as described in Example 3.
Figure 8:
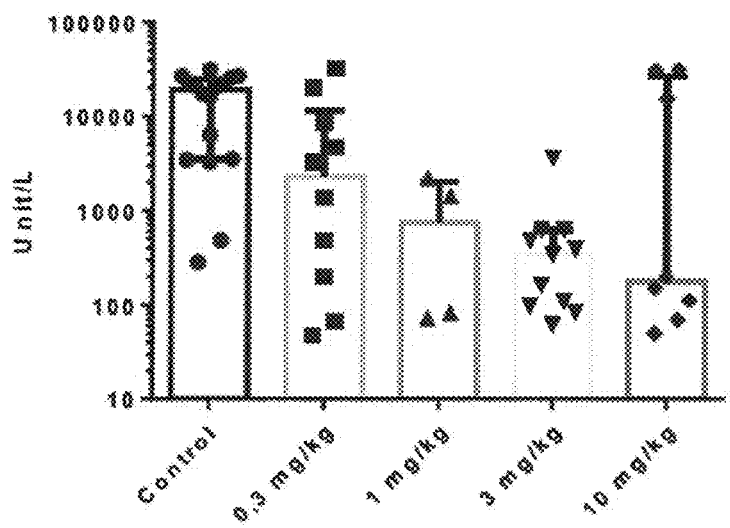
FIG. 8 shows the median±interquartile ALAT levels at 12 hours following i.p. injection of acetaminophen in male B6C3F1 mice which were also administered a calmangafodipir (CaM) dosage of 0.3-10 mg/kg CaM 6 hours post acetaminophen administration (n=4-16 per bar), as described in Example 3.

FIGS. 6 to 8 show ALF response to administration of NAC and CaM, as detected by monitoring ALAT. Specifically, FIG. 6 shows Mean±SEM ALAT levels at 12 hours following the i.p. injection of 300 mg/kg acetaminophen in male B6C3F1 mice (n=4-32 per bar), which were also administered 300 mg/kg NAC 1-6 hours after acetaminophen administration. In the figure, NS refers to statistically not significantly different from control data while *** refers to the data being $p<0.001$, and * refers to the data being $p<0.05$, statistically significant from control data. FIG. 7 indicates the NAC dose-response of NAC administration of 30-300 mg/kg NAC 1 hour post acetaminophen administration. Mean t SEM ALAT levels at 12 hours following i.p.

injection of 300 mg/kg acetaminophen in male B6C3F1 mice (n=4-11 per bar) are shown. No clear dose-response could be detected. FIG. 8 shows the CaM dose response of administration of 0.3-10 mg/kg calmangafodipir (CaM) 6 hours post acetaminophen administration of 300 mg/kg acetaminophen. Median±interquartile ALAT levels at 12 hours following i.p. injection of acetaminophen in male 86C3F1 mice (n=4-16 per bar) are shown. Due to some outlier values, and variability from the two experiments, both of which are not unexpected in such model system studies, the data points are plotted individually as well as the median values±inter-quartile range.

Example 4

This Example studied the pharmaceutical effects of individual and combined therapies on animal deaths and involved male B6C3F1 mice. Even though serum enzyme activity studies are strongly indicative of liver failure or protection, it is also important to consider other data such as that related to subject animal deaths (%) as a function of the pharmacological treatment. The experiments of this Example studied the pharmaceutical effects of individual and combined therapies on animal deaths in male B6C3F1 mice. The mice were fasted for 8-10 hours and ALF was induced with 300 mg/kg acetaminophen (APAP), i.p., with treatment as specified in the following test groups:

APAP control (n=81, APAP 300 mg/kg i.p.),
NAC (n=53, 30-300 mg/kg i.v., 1-6 hours post APAP),
CaM (n=97, 0.3-10 mg/kg i.v., 1-6 hours post APAP),
CaDPDP (n=10, 3-10 mg/kg i.v., 6 hours post APAP), and
NAC/CaM (n=28, NAC 300 mg/kg, combined with 0.3-10 mg/kg CaM i.v., 2.5-6 hours post APAP).

Table 1 shows the relative number of deaths (%) within the 12 hour sampling period as a function of the pharmacological treatment. The highest number of deaths was seen in the chelator group without a manganese component (CaDPDP). Surprisingly, a lower number of deaths than expected was seen for the combination of NAC and CaM, compared with either NAC or CaM alone or with the APAP control.

TABLE 1

| Treatment | APAP | NAG | CaM | CaDPDP | NAC/CaM |
|---|---|---|---|---|---|
| Total (n) | 81 | 53 | 97 | 10 | 28 |
| Deaths, no. | 12 | 4 | 8 | 3 | 1 |
| Deaths, % | 15% | 8% | 8% | 30% | 4% |

More specifically, spontaneous deaths in the ALF-sensitive mice undergoing acetaminophen overdose were fairly equally distributed between the acetaminophen overdose (untreated) control (15%) and the NAC (8%) or calmangafodipir (8%) treatments groups. However, a clear tendency for fewer deaths was seen in the NAC plus calmangafodipir combination treatment group (1/28; 4%). This result was not predictable based on the results seen when NAC or CaM were administered alone (Table 1), and the relatively low amount of SOD mimetic per dose caused by combining NAC with CaM in the indicated amounts, and also in view of the results presented in FIG. 6. This interesting result appears particularly related to CaM as witnessed by the highest numbers of deaths being seen in the CaDPDP chelator compound groups lacking a manganese component (CaDPDP, 3/10; 30%).

The specific embodiments and examples described herein are exemplary only in nature and are not intended to be limiting of the invention defined by the claims. Further embodiments and examples, and advantages thereof, will be apparent to one of ordinary skill in the art in view of this specification and are within the scope of the claimed invention.

What is claimed is:

1. A method of treating and/or protecting against acute liver failure induced by an acetaminophen overdose in an individual, comprising
   (a) intravenously administering to the individual a solution comprising from about 100 to 500 mg/kg body weight of a first active agent comprising N-acetylcysteine (NAC), and
   (b) intravenously administering to the individual a solution comprising from about 0.3 to 10 mg/kg body weight of a second active agent comprising a manganese complex selected from the group consisting of
      (i) calmangafodipir, or a pharmaceutically acceptable salt thereof, and
      (ii) a mixture of manganese N,N'-bis-(pyridoxal-5-phosphate)-ethylenediamine-N, N'-diacetic acid (MnDPDP), or a pharmaceutically acceptable salt thereof, and calcium N,N'-bis-(pyridoxal-5-phosphate)-ethylenediamine-N, N'-diacetic acid (CaDPDP), or pharmaceutically acceptable salt thereof, in an approximate calcium to manganese molar ratio of 4:1,
   wherein the administration of the first active agent and the administration of the second active agent are each at a time 8 hours or more subsequent to the acetaminophen overdose.

2. The method of claim 1, wherein the weight ratio of the first active agent to the second active agent is in a range of from 300:1 to 1:1.

3. The method of claim 1, wherein the first active agent and the second active agent are administered substantially simultaneously to the individual.

4. The method of claim 3, wherein the first active agent and the second active agent are administered in a single formulation.

5. The method of claim 1, wherein the solution of the second active agent is formed from a freeze-dried formulation of the second active agent.

6. The method of claim 3, wherein an additional dosage of the second active agent is administered subsequent to the substantially simultaneous administration of the first active agent and the second active agent.

7. The method of claim 1, wherein the first active agent and the second active agent are administered separately to the individual.

8. The method of claim 7, wherein the second active agent is administered to the individual subsequent to administration of the first active agent.

9. The method of claim 7, wherein the second active agent is administered to the individual prior to administration of the first active agent.

10. The method of claim 1, wherein, prior to administration of the first active agent or the second active agent, the individual has been determined to be in need of a treatment to reduce the probability of oxidative stress leading to hepatocyte cell death.

11. The method of claim 10, wherein the individual has been determined to be in need of a treatment by determining a level of at least one biomarker indicative of a risk of developing acute liver failure induced by an acetaminophen overdose.

12. The method of claim 1, wherein the weight ratio of the first active agent to the second active agent is in a range of from 50:1 to 1:1.

13. The method of claim 1, wherein the weight ratio of the first active agent to the second active agent is in a range of from 20:1 to 1:1.

14. The method of claim 1, wherein the second active agent comprises a pharmaceutically acceptable salt of calmangafodipir.

15. The method of claim 1, wherein the second active agent comprises a pharmaceutically acceptable sodium salt of calmangafodipir.

16. A method of treating and/or protecting against acute liver failure induced by an acetaminophen overdose in an individual, comprising
   (a) intravenously administering to the individual a solution comprising from about 100 to 500 mg/kg body weight of a first active agent comprising N-acetylcysteine (NAC), and
   (b) intravenously administering to the individual a solution comprising from about 0.3 to 25 mg/kg body weight of a second active agent comprising a manganese complex selected from the group consisting of
      (i) calmangafodipir, or a pharmaceutically acceptable salt thereof, and
      (ii) a mixture of manganese N,N'-bis-(pyridoxal-5-phosphate)-ethylenediamine-N,N'-diacetic acid (MnDPDP), or a pharmaceutically acceptable salt thereof, and calcium N,N'-bis-(pyridoxal-5-phosphate)-ethylenediamine-N, N'-diacetic acid (CaDPDP), or pharmaceutically acceptable salt thereof, in an approximate calcium to manganese molar ratio of 4:1,
   wherein the weight ratio of the first active agent to the second active agent is in a range of from 300:1 to 1:1, and wherein the administration of the first active agent and the administration of the second active agent are each at a time 8 hours or more subsequent to the acetaminophen overdose.

17. The method of claim 16, wherein the first active agent and the second active agent are administered separately to the individual.

18. The method of claim 16, wherein the weight ratio of the first active agent to the second active agent is in a range of from 50:1 to 1:1.

19. The method of claim 16, wherein the second active agent comprises a pharmaceutically acceptable salt of the manganese-containing compound of (i) or (ii).

20. The method of claim 1, wherein the second active agent is (ii) the mixture of MnDPDP, or a pharmaceutically acceptable salt thereof, and CaDPDP or a pharmaceutically acceptable salt thereof.

21. The method of claim 20, wherein the second active agent is a mixture a sodium salt of MnDPDP and a sodium salt of CaDPDP DPDP.

* * * * *